Figure 1:
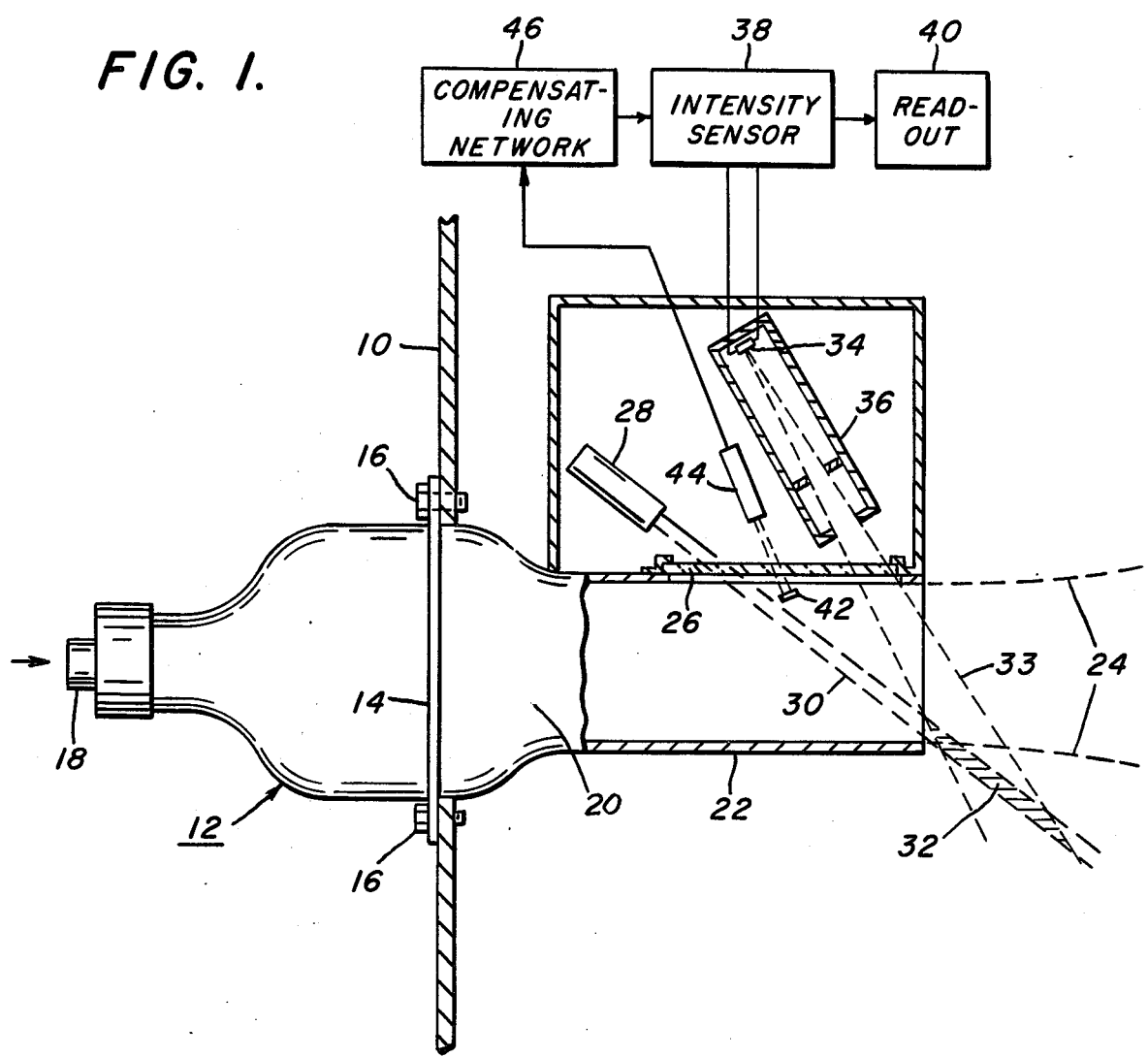

United States Patent [19]

Malone

[11] 4,155,651
[45] May 22, 1979

[54] APPARATUS FOR MEASURING THE TOTAL MASS OF PARTICLES SUSPENDED IN A FLUID

[75] Inventor: Erle W. Malone, Seattle, Wash.

[73] Assignee: The Boeing Company, Seattle, Wash.

[21] Appl. No.: 851,039

[22] Filed: Nov. 14, 1977

[51] Int. Cl.² .................... G01N 21/22; G01N 21/26
[52] U.S. Cl. .................................. 356/342; 356/341; 350/63; 250/574
[58] Field of Search ............. 356/103, 201, 207, 209, 356/104; 350/63, 61; 250/574; 340/628, 630

[56] References Cited

U.S. PATENT DOCUMENTS

| 4,018,513 | 4/1977 | Boeke .................................. 350/319 |
| 4,024,407 | 5/1977 | Merk et al. ........................... 356/207 |

FOREIGN PATENT DOCUMENTS 1003661  1/1977  Canada .................................. 356/103

OTHER PUBLICATIONS

Elijah, et al, "Temperature Sensing", *IBM Technical Disclosure Bulletin* vol. 13, No. 3, Aug. 1970.

*Primary Examiner*—John K. Corbin
*Assistant Examiner*—Bruce Y. Arnold
*Attorney, Agent, or Firm*—Thomas H. Murray

[57] ABSTRACT

Optical apparatus for measuring the amount of light reflected and/or scattered by particles suspended in a fluid, such as scrubber carryover appearing as a spray of dispersed water droplets. The amount of light reflected and/or scattered is an indication of the volume and mass of the suspended particles. A beam of light is caused to pass diagonally across a stream of purging gas used to keep the optical components clean and is directed onto the suspended particles at a point outside the purging gas stream. The light reflected back through the purging stream is then measured in intensity to determine the total volume of the particles from which mass may be determined. The invention overcomes the disadvantages of prior art devices in which the purging gas can disrupt the environment in which particle density is to be measured.

6 Claims, 2 Drawing Figures

U.S. Patent
May 22, 1979
4,155,651

APPARATUS FOR MEASURING THE TOTAL MASS OF PARTICLES SUSPENDED IN A FLUID

BACKGROUND OF THE INVENTION

While not limited thereto, the present invention is particularly adapted for use in measuring the amount of scrubber carryover moisture appearing as a spray of dispersed water droplets. Such scrubbers are used, for example, to remove pollutants from the flue gases of coal-fired power plants. In the scrubber, the flue gases entrain liquor (i.e., water) droplets; and this water must be vaporized before the flue gases pass to the atmosphere. The amount of carryover moisture seriously affects the efficiency of a coal-fired power plant since, in order to vaporize the water droplets entrained in the flue gases, they must pass through steam coils or other heating apparatus which can use up to 5% of the total heat generated by the power plant. Accordingly, it is preferable to use some means for monitoring the carryover moisture level in order that the operating parameters of the scrubber can be optimized to minimize the water content of the scrubbed gas.

In the past, attempts have been made to measure carryover moisture with the use of see-through opacity devices such as smoke detectors and back-scattered laser beam single particle detectors. These devices, however, have met with only limited success. Each requires a stream of purging gas to keep the optical components clean, but the purging gas disturbs the environment in which measurements are taken, usually causing a low indication of particle mass. Additionally, high particle density can saturate the light detector primarily because of the fact that a very small finite field-of-view is employed in an attempt to isolate a single water droplet in the environment.

SUMMARY OF THE INVENTION

In accordance with the present invention, the limitations of prior art moisture detectors are obviated by utilizing a device which employs a light beam and collector directed at an angle to the purging gas flow by using a relatively wide angle light detector to detect the reflected and/or backscattered light.

Specifically, there is provided apparatus for detecting and measuring the amount of light scattered by particles suspended in a fluid entrained within an enclosure comprising a purging tube which extends into the enclosure, together with means for directing a purging gas through the tube and into the enclosure. Optical apparatus is provided for forming a beam of light extending diagonally across the purging tube and directed onto particles suspended in the fluid within the enclosure beyond the end of the purging tube and outside the path of travel of the purging gas. Light reflected and/or backscattered from the particles within the fluid, passing through the stream of purging gas, is then detected and measured in intensity. In this manner, the backscattered light is derived from an area within the enclosure which is unmixed with the purging gas stream such that a true and accurate measurement of total particle mass density can be derived.

The beam of light which passes through the purging tube and into the environment containing moisture may be collimated. In one embodiment of the invention, a collimated light source and a light detector are disposed outside the purging tube, the light passing into and out of the purging tube through a transparent wall portion of the tube. In another embodiment, the collimated light source and the light detector are disposed within the purging tube itself. In this embodiment, mirrors are employed to direct the collimated light beam into the environment containing moisture and to direct the backscattered light to a light sensor.

Figure 2:
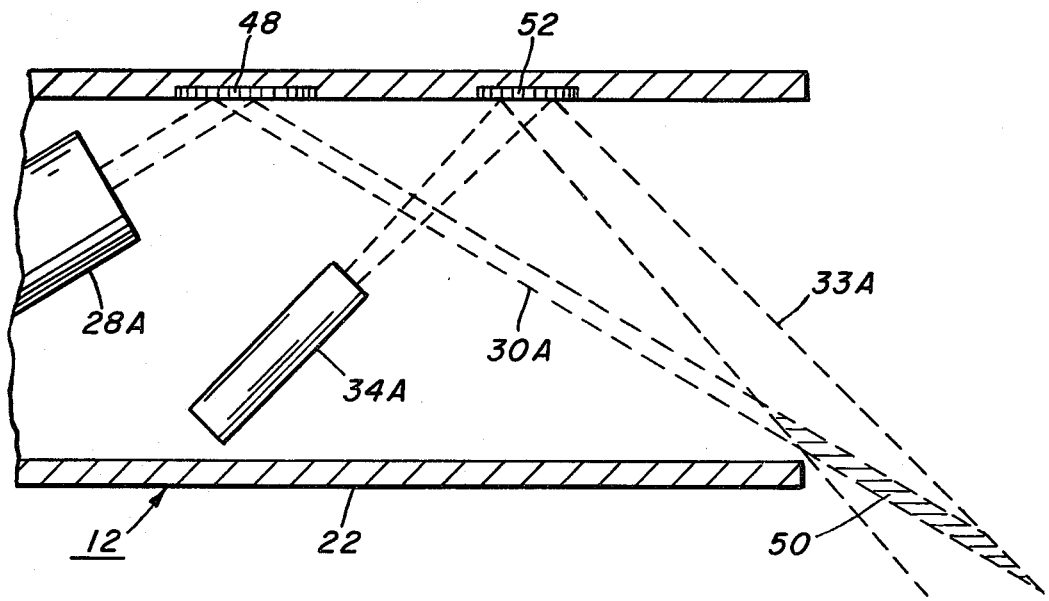

The above and other objects and features of the invention will become apparent from the following detailed description taken in connection with the accompanying drawings which form a part of this specification, and in which:

FIG. 1 is an illustration of one embodiment of the invention wherein a light sensor and source of collimated light are disposed outside a purging tube extending into a scrubber; and FIG. 2 is a schematic illustration of another embodiment of the invention wherein the light source and light detector are disposed directly within the purging tube itself.

With reference now to the drawings, and particularly to FIG. 1, the numeral 10 designates the wall of a gas scrubber through which flue gases from a power generating plant, for example, pass. As they pass through the scrubber, they become laden with water droplets. As was explained above, it is necessary to evaporate these water droplets before the flue gases pass to the atmosphere. Therefore, it is desirable to maintain the density of the entrained water droplet volume at a point at which efficient scrubbing is achieved and below a point at which the system becomes overloaded and requires excessive heat for evaporation.

One embodiment of the apparatus of the invention for maintaining such moisture is shown in FIG. 1 and includes a purging tube 12 extending through the wall 10 of the scrubber and secured thereto by means of a flange 14 and bolts 16; although any fastening means can be utilized to effect sealing engagement between the purging tube and an opening in the scrubber wall 10. In some scrubber systems, a negative pressure exists within the scrubber such that air will be sucked into the purging tube 12 through an opening 18 and thence into a plenum chamber 20 where laminar flow of the purging air is achieved. From the plenum chamber 20, the purging air passes through a cylindrical portion 22 of the purging tube and thence into the interior of the scrubber, the path of the purging air being defined generally by the broken lines 24. If necessary, purge gas under pressure can be forced through the opening 18 when the scrubber operates under positive pressure.

As shown in FIG. 1, the cylindrical portion 22 has a transparent wall portion 26; and above the transparent wall portion 26 is a light beam generator 28. The generator 28 produces a light beam 30 which passes diagonally across the cylindrical portion 22 and into the scrubber where it intersects moisture droplets generally in the area 32. Light backscattered from the moisture droplets in the area 32 along path 33 is then detected by silicone diode 34 or the like within a housing 36, the backscattered light also passing diagonally across the cylindrical portion 22 and through the transparent wall portion 26.

The silicone diode 34, in turn, is connected to a suitable intensity detector 38, the intensity of the light thus detected being indicated on a suitable readout device 40. Since the backscattered light sensed by the diode 34 is derived from an area within the scrubber which is not affected by the purging air stream, the readout derived from the intensity sensor 38 is a true indication of the moisture content of the gaseous atmosphere within the scrubber unaffected by the purging air stream.

The purpose of the purging air stream, of course, is to keep the underside of the transparent plate 26 clean. In case the transparency of the plate 26 should vary, however, a mirror 42 is placed within the cylindrical portion 22 such that it intersects a small portion of the collimated light beam 30. The portion of the light intersected is reflected back to a second light detector 44 which, in turn, is connected to a compensating network 46. The compensating network 46 acts to vary the parameters of the intensity sensor 38 such that the reading obtained from the readout 40 will be constant for any given moisture content density regardless of whether the transparency of the plate 26 varies.

In FIG. 2, another embodiment of the invention is shown wherein elements corresponding to those of FIG. 1 are identified by like reference numerals. In this case, the cylindrical portion 22 of purging tube 12 does not contain a transparent wall portion. Rather, the light beam generator 28A and light sensor 34A are located directly within the purging tube. Light from the light beam generator 28A is reflected from a first mirror 48 diagonally across the cylindrical portion 22 and into the area 50 within the scrubber and outside the path of the purging air stream passing through the tube 12. Backscattered light is then reflected from the area 50 via mirror 52 back to the light sensor 34A. The light sensor 34A, in turn, is connected to a suitable intensity sensor such as sensor 38 in FIG. 1. If desired, a compensating mirror and light detector, such as mirror 42 and sensor 44 of FIG. 1 may be arranged to sense the intensity of the light beam 30A in order to compensate for any variation in the reflectivity of the mirror 48 or the transparency of the lens of the light beam generator 28A.

Although the invention has been shown in connection with certain specific embodiments, it will be readily apparent to those skilled in the art that various changes in form and arrangement of parts may be made to suit requirements without departing from the spirit and scope of the invention.

I claim as my invention:

1. Apparatus for detecting and measuring the amount of light scattered by particles suspended in a fluid entrained within an enclosure comprising a purging tube extending into said enclosure, means for directing a purging gas through the purging tube and into the enclosure, means for forming a beam of light extending diagonally across the purging tube and directed onto particles suspended in the fluid within the enclosure beyond the end of the purging tube and outside the path of travel of said purging gas, and means for detecting light reflected and/or backscattered from said particles.

2. The apparatus of claim 1 wherein said means for forming a beam of light comprises a light beam generator having an axis disposed at an angle less than 90° with respect to the path of travel of said purging gas.

3. The apparatus of claim 2 wherein said means for detecting light has a field-of-view with an axis disposed at an angle less than 90° with respect to the path of travel of said purging gas.

4. Apparatus for detecting and measuring the amount of light scattered by particles suspended in a fluid entrained within an enclosure comprising a purging tube extending into said enclosure, means for directing a purging gas through the purging tube, at least a portion of the wall of said purging tube being formed from light-transparent material, means for directing a beam of light through said transparent portion of the wall and diagonally across the purging tube onto particles suspended in the fluid within the enclosure outside the path of travel of said purging gas, and means for detecting light reflected and/or backscattered from said particles and passing through said transparent portion of the tube.

5. Apparatus for detecting and measuring the amount of light scattered by particles suspended in a fluid entrained within an enclosure comprising a purging tube extending into said enclosure, means for directing a purging gas through the purging tube, first and second mirrors spaced along the wall of said purging tube, means for directing a beam of light against one of said mirrors where it is reflected diagonally across the purging tube and onto particles suspended in the fluid within the enclosure beyond the end of the purging tube and outside the path of travel of said purging gas, and means for detecting light reflected and/or backscattered from said paticles and reflected from the second of said mirrors.

6. The apparatus of claim 5 wherein said means for directing a beam of light and said means for detecting light are disposed within the purging tube.

* * * * *